(12) United States Patent
Jiang et al.

(10) Patent No.: US 11,278,507 B2
(45) Date of Patent: Mar. 22, 2022

(54) METHOD OF REGULATING IMMUNITY IN THE INTESTINES

(71) Applicant: Monell Chemical Senses Center, Philadelphia, PA (US)

(72) Inventors: Peihua Jiang, Clarksville, MD (US); Weiwei Lei, Berwyn, PA (US)

(73) Assignee: Monell Chemical Senses Center, Philadelphia, PA (US)

(*) Notice: Subject to any disclaimer, the term of this patent is extended or adjusted under 35 U.S.C. 154(b) by 465 days.

(21) Appl. No.: 16/330,595

(22) PCT Filed: Aug. 21, 2017

(86) PCT No.: PCT/US2017/047783
§ 371 (c)(1),
(2) Date: Mar. 5, 2019

(87) PCT Pub. No.: WO2018/048609
PCT Pub. Date: Mar. 15, 2018

(65) Prior Publication Data
US 2021/0283079 A1   Sep. 16, 2021

Related U.S. Application Data

(60) Provisional application No. 62/383,662, filed on Sep. 6, 2016.

(51) Int. Cl.
*A61K 31/194* (2006.01)
(52) U.S. Cl.
CPC .................. *A61K 31/194* (2013.01)
(58) Field of Classification Search
CPC .................................................. A61K 31/194
USPC ........................................................ 514/574
See application file for complete search history.

(56) References Cited

U.S. PATENT DOCUMENTS

| | | |
|---|---|---|
| 2001/0031748 A1 | 10/2001 | Thompson et al. |
| 2006/0134109 A1 | 6/2006 | Gaitanaris et al. |
| 2006/0173078 A1 | 8/2006 | McGregor |
| 2009/0317827 A1 | 12/2009 | Carballido Herrera et al. |
| 2015/0038414 A1 | 2/2015 | Lambert |

FOREIGN PATENT DOCUMENTS

WO    WO2005/050220 A1    6/2005

OTHER PUBLICATIONS

Connors, J., et al., The Role of Succinate in the Regulation of Intestinal Inflammation, Nutrients, 2019, 11(1):25, epub Dec. 22, 2018.

Gerbe, F. et al, Intestinal epithelial tuft cells initiate type 2 mucosal immunity to helminth parasites. Nature, 529 (7585):226-230 (Jan. 2016).
Hamel, D. et al, G-Protein-Coupled Receptor 91 and Succinate are Key Contributors in Neonatal Postcerebral Hypoxia-Ischemia Recovery. Arterioscler Thromb Vasc. Biol. (Feb. 2014), vol. 34(2):285-93.
Spellberg, B. and Edwards, JE Jr., Type 1/Type 2 immunity in infectious diseases. Clin Infect Dis., 32(1),:76-102 (Jan. 2001).
Pearce et al., Metabolic Pathways in Immune Cell Activation and Quiescence. Immunity. 38(4): 633-43 (Apr. 2013).
Wang, Y-H et al., IL-25 augments type 2 immune responses by enhancing the expansion and functions of TSLP-DC-activated Th2 memory cells. J Exp Med. 204(8):1837-47 (Aug. 2007).
Rubic-Schneider, T et al., GPR91 deficiency exacerbates allergic contact dermatitis while reducing arthritic disease in mice. Allergy, 72(3): 444-452 (2017. Epub Sep. 12, 2016).
Aguiar, CJ et al, Succinate causes pathological cardiomyocyte hypertrophy through GPR91 activation. Cell Commun. Signaling, 12:78 (Dec. 2014).
Bhuniya, D. et al, Discovery of a potent and selective small molecule hGPR91 antagonist, Bioorg. Medic. Chem. Lett., 21:3596-3602 (Apr. 2011).
De Castro Fonseca, M et al., GPR91: expanding the frontiers of Krebs cycle intermediates, Cell Commun. Signaling, 14:3 (Jan. 2016).
Ariza, AC et al, The succinate receptor as a novel therapeutic target for oxidative and metabolic stress-related conditions. Frontiers in Endocrinol., 3(22):1-8 (Feb. 2012).
Howitt, MR et al, Tuft cells, taste-chemosensory cells, orchestrate parasite type 2 immunity in the gut. Science, 10.1126/science. aaf1648 (Feb. 2016).
Lei, W et al, Activation of intestinal tuft cell-expressed Sucnr1 triggers type 2 immunity in the mouse small intestine. Proc. Natl. Acad. Sci., USA, 115(21):5552-5557 (May 2018).
McCreath, KJ et al., Targeted Disruption of the SUCNR1 Metabolic Receptor Leads to Dichotomous Effects on Obesity. Diabetes, 64:1154-1167 (Apr. 2015).
Millholland, MG et al., A Host GPCR Signaling Network Required for the Cytolysis of Infected Cells Facilitates Release of Apicomplexan Parasites. Cell Host Microbe., 13(1):15-28 (Jan. 2013).
Taguet, N. et al, Inflammatory Bowel Disease G-Protein Coupled Receptors (GPCRs) Expression Profiling with Microfluidic Cards, Crohn's Disease, Dr. Sami Karoui (Ed.), ISBN: 978-953-307-811-3, (Jan. 2012).
Toma, I et al, Succinate receptor GPR91 provides a direct link between high glucose levels and renin release in murine and rabbit kidney., J. Clin. Invest., 118(7):2526-2534 (Jul. 2008).
Von Moltke, J et al., Tuft-cell-derived IL-25 regulates an intestinal ILC2-epithelial response circuit. Nature, 529:221-5 (Dec. 14).

(Continued)

*Primary Examiner* — Kristin A Vajda
(74) *Attorney, Agent, or Firm* — Howson & Howson LLP; Colleen Schaller

(57) ABSTRACT

Methods for stimulating the G protein receptor (Gpr91) pathway in intestinal cells to release IL-25 and enhance a type II immune response in the subject are useful in the treatment or prevention of bacterial or parasitic infection. Similarly methods and compositions used therein to inhibit or stimulate GPR91 are useful for the treatment or inhibition of certain diseases, such as irritable bowel syndrome (IBS), inflammatory bowel disease (IBD), and Crohn's disease.

4 Claims, 2 Drawing Sheets

(56) References Cited

OTHER PUBLICATIONS

Xu, J et al, The MAPK signaling pathway mediates the GPR91-dependent release of VEGF from RGC-5 cells. Internatl. J. Mol. Medic., 36:130-138 (Jul. 2015).
"GPCR Targets by Therapeutic/Disease Area", retrieved from https://www.discoverx.com/targets/gpcr-target-biology/gpcr-targets-by-therapeutic-disease-area on Mar. 6, 2019, 3 pages.
International Search Report and Written Opinion dated Nov. 28, 2017 in corresponding International Patent Application PCT/US2017/047783, filed Aug. 21, 2017.

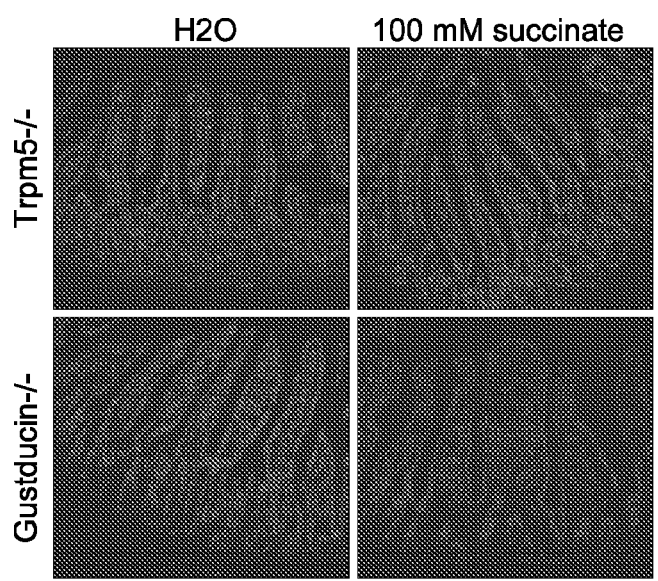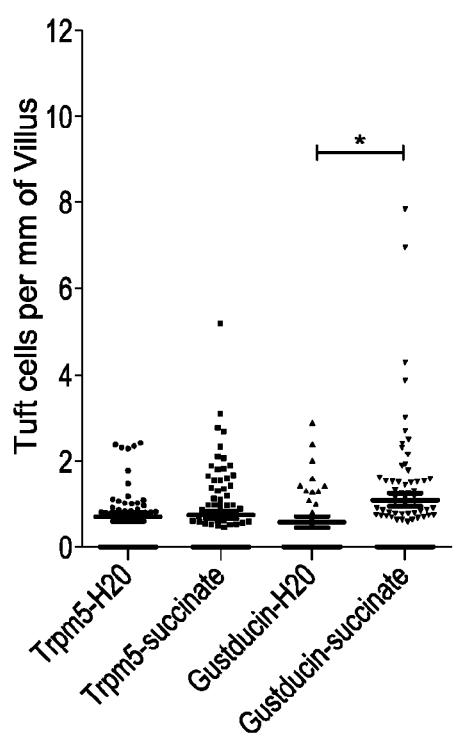
FIG. 2A  FIG. 2B

METHOD OF REGULATING IMMUNITY IN THE INTESTINES

CROSS-REFERENCE TO RELATED APPLICATIONS

This application is a national stage of International Patent Application No. PCT/US2017/047783, filed Aug. 21, 2017, which claims the benefit of the priority of U.S. Provisional Patent Application No. 62/383,662, filed Sep. 6, 2016, which applications are incorporated herein by reference.

BACKGROUND OF THE INVENTION

A variety of ailments of the gastrointestinal tract are caused by microorganisms such as parasites and bacteria. Such disorders range from gastroenteritis and gastritis to ulcers, ulcerative colitis and more serious auto-immune diseases such as Crohn's disease.

Present methods for treating such disorders involve administration of anti-parasitic or antibiotic drugs that have significant side effects. Other compositions and methods are needed to treat such disorders by impacting the underlying biochemical pathways that can cause, enhance or inhibit such disease.

SUMMARY OF THE INVENTION

The following methods and compositions are based upon the inventors' determinations and evidence that intestinal tuft cells may rely on the succinate-Gpr91 axis to detect and fight parasitic and bacterial infections.

In one aspect, a method for triggering release of a type II immune response by intestinal cells comprises contacting cells of the intestine with a composition or compound that stimulates the G protein receptor (Gpr91) pathway, i.e., a GPR91 agonist. In one embodiment, the method involves contacting the cells in the presence of gustducin or Trpm.

In another aspect, a method comprises administering to a mammalian subject at risk for, or having, an infection, such as a parasitic or bacterial infection, a composition or compound that stimulates the G protein receptor (Gpr91) pathway in intestinal cells to release IL-25 and enhance a type II immune response in the subject. In still other embodiments, the cells being contacted or treated in these methods are tuft cells.

In another aspect, method of treating ulcerative disorders of the intestines comprises administering to a subject having an ulcerative disorder a composition or compound that blocks tuft cell-expressed Gpr91 or the Gpr91 pathway and inhibits release of IL-25. In one embodiment, the disease is Crohn's disease or Irritable Bowel Syndrome.

In another aspect, a method of treating obesity comprises administering to an obese subject a composition or compound that stimulates the Gpr91 pathway in intestinal cells and releases IL-25.

In another embodiment, a method for detecting parasitic or other microbial infection of the gastrointestinal tract involves testing a subject for increased production of IL-25, released by stimulated tuft cells.

Other aspects and advantages of the invention will be readily apparent from the following detailed description of the invention.

BRIEF DESCRIPTION OF THE DRAWINGS

FIG. 2A demonstrates that succinate-induced tuft cell hyperplasia requires gustducin and Trpm5. Jejunal sections from gustducin and Trpm5 knockout mice drinking plain water or succinate-containing water for 7 days. Tuft cells (which appear as grey dots) were detected by staining with an anti-Dclk1 antibody.

FIG. 2B is a graph showing the statistical analysis of tuft cell expansion, which showed a small but significant increase in the number of tuft cells after succinate treatment in gustducin KO mice but not in Trpm5 KO mice (p=0.0277, t-test).

DETAILED DESCRIPTION OF THE INVENTION

Figure 1A:
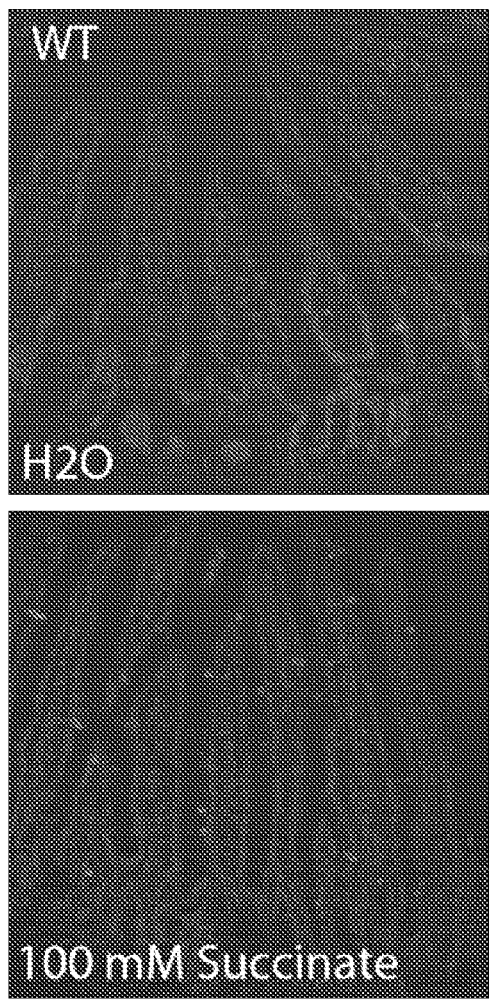
FIG. 1A demonstrates succinate induced tuft cell hyperplasia. Jejunal sections from wildtype mice drinking plain water or succinate-containing water for 7 days. Tuft cells (which appear as a few light gray dots in the right lower corner) were detected by staining with an anti-Dclk1 antibody.

In the small intestine, the epithelium consists of at least five distinct cellular lineages, including the tuft cell, whose function is unclear. Parasitic helminths, certain bacterial infections, and allergens induce a type 2 immune response leading to profound changes in intestinal tissue physiology. Tuft cells, tissue-resident ILC2 cells, and epithelial progenitor cells constitute a feedback loop that mediates epithelial remodeling associated with type 2 immunity in the small intestine. A hallmark feature of tuft cell-mediated type 2 immunity is tuft cell hyperplasia, which is an increase in the number of cells. Hyperplasia of mucus-secreting goblet cells and smooth muscle hypercontractility also occur in response to the type 2 immune response. These responses require interleukin (IL)-13 production by tissue-resident group 2 innate lymphoid cells (ILC2s) and recruited type 2 helper T cells (T H2 cells) (von Moltke J. et al, 2016 January, Nature, 529:221-225). The sources and regulation of these signals remain poorly defined.

Previous microarray-based transcriptome analysis showed that tuft cells express the succinate receptor Gpr91. Parasite or microbe infection can produce succinate, i.e., a metabolite of the tricarboxylic acid (TCA) cycle, under anaerobic conditions. However, how tuft cells detect and respond to pathogens such as parasites or microbes remains largely unknown.

The methods and compositions described herein are based upon the inventors' discovery that the Gpr91 receptor in tuft intestinal cells can be manipulated by certain agonists or antagonists to activate or block type II immunity in the gut. Assays for screening compounds that stimulate or block Gpr91 are available as described herein. These assays and components of the assays, such as cell lines and recombinant cells, are provided for screening Gpr91 agonists/antagonists that are useful in modulating Gpr91 type II immunity to repair or remodel intestinal tissue or to treat diseases such as Crohn's disease, IBS, and obesity, among others.

Without wishing to be bound by theory, the inventors hypothesize that intestinal tuft cells sense succinate through Gpr91 to trigger release of IL-25, which further initiates parasite type II immunity. As described in the examples below, the inventors found that succinate can induce tuft cell hyperplasia in wild-type mice, a hallmark feature of type II immunity in response to parasitic infections. Succinate-induced tuft cell hyperplasia is dependent on tuft cell-expressed chemosensory signaling elements gustducin and Trpm5. In the absence of gustducin or Trpm5, succinate does not induce tuft cell hyperplasia. Thus, intestinal tuft cells rely on the succinate-Gpr91 axis to detect and fight parasitic and bacterial infections.

Definitions and Components Used in the Methods

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

Various embodiments in the specification are presented using "comprising" language, which is inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

The term "about" as used herein when referring to a measurable value such as an amount, a temporal duration, and the like, is meant to encompass variations of up to ±10% from the specified value; as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."

By "mammalian subject" is meant primarily a human, but also domestic animals, e.g., dogs, cats; and livestock, such as cattle, pigs, etc.; and common laboratory mammals, such as primates, rabbits, and rodents; and pest or wild animals, such as deer, rodents, rabbits, squirrels, etc.

By "GPR91" is meant the seven transmembrane G protein coupled receptor or succinate receptor encoded in humans by the nucleic acid (mRNA) sequence shown in GenBank Accession No. AF348078 and NCBI database accession No. NM_033050.5. The GPR91 or SUCR1 amino acid sequences are provided by the NCBI database Accession No. NP_149039 or Genbank database by Accession No. AAK29080.1. These sequences are incorporated by reference herein.

The terms "compound", "composition", or "molecule" as used herein may be used interchangeably to discuss the form of the GPR91 agonists or antagonists useful in these methods. By "pharmaceutical compositions" is meant the compound (GPR91 agonist or antagonist) as an active ingredient in a formulation with a pharmaceutically acceptable carrier, vehicle or excipient. The pharmaceutical compositions may also be formulated to suit a selected route of administration, and may contain ingredients specific to the route of administration as known to one of skill in the art of pharmaceutical formulation.

By "GPR91 agonist or antagonist(s)" as used herein is meant a compound, molecule (synthetic or natural) or a composition comprising multiple compounds or molecules) that modify the activation, nucleic acid expression, protein expression, signaling or activity of the GPR91 receptors or an intermediate in the signaling pathway thereof. In one embodiment the agonist or antagonist(s) operates in all cells in which GPR91 is present. In another embodiment, the ligand/modifier(s) is specific for modifying GPR91 in the subject's intestinal cells or tuft cells. In one embodiment, the GPR91 agonist decreases, inhibits, blocks or down-regulates the activation, expression, signaling or activity of the receptor, particular the expression of IL-25 by the cells. In another embodiment, the GPR91 agonists or antagonist (s) provides, increases or up-regulates the activation, expression, signaling or activity of GPR91 receptor, particular the expression of IL-25 by the cells. In another embodiment, the agonist/antagonist(s) exerts in modifying action on a single GPR91 receptor or intermediate or on multiple GPR91 receptors or intermediates.

Among such GPR91 agonist/antagonist compositions or compounds useful in the methods described herein are succinate and analogs of succinate. By "analogs of succinate" are included other structural derivatives of succinate ($C_4H_4O_4$) that can differ by one or more elements. In certain embodiments, esters, amides and one-carbon-homologs of succinate are analogs. Also included are malonate, succinate dehydrogenase, alpha-tocopheryl succinate, and the like. Other compounds that are anticipated to be useful as GPR91 agonist/antagonists include those identified in, or by the assays described in, PCT International Publication Nos. WO 2005/010152; WO 2005/050220; WO 2006/117193 and WO 2009/011885 incorporated herein by reference. In one embodiment, as shown in the examples below, the agonist is succinate or an analog thereof. In another embodiment Gpr91 antagonists include those small molecules antagonists described in Bhuniya, D. et al, 2011, Bioorganic & Medicinal Chem. Lett., 21:3596-3602, incorporated herein by reference. Any of such molecules could potentially stimulate/activate or inhibit/suppress GPR91 activity are potentially useful in the methods described herein. Similarly mammal-specific small molecule agonists/antagonists of GPR91 or its intermediates may be readily identified from libraries of various chemical compounds.

By the term "pharmaceutically acceptable carrier or vehicle" is meant a solution or suspension that is safe for human administration. Optionally such carriers enhance stability and/or immunogenicity. Such carriers include, for example, water, saline, buffered saline, alcohols, gum Arabic, vegetable oils, benzyl alcohols, polyethylene glycols, gelatin, carbohydrates, such as lactose, amylase or starch, magnesium stearate, talc, silicic acid, viscous paraffin, perfume oil, fatty acid monoglycerides and diglycerides, pentaerythritol fatty acid esters, hydroxymethylcellulose, polyvinylpyrrolidone, liposomes, oil in water emulsions and others. The compositions may further include a detergent to make the peptide more bioavailable, e.g., octylglucoside. The compositions and compounds useful in the methods may be administered to a patient, preferably suspended in a biologically compatible solution or pharmaceutically acceptable delivery vehicle. The various components of the methods are prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. Other aqueous and non-aqueous isotonic sterile injection solutions and aqueous and non-aqueous sterile suspensions known to be pharmaceutically acceptable carriers and well known to those of skill in the art may be employed for this purpose.

By "administering" or "route of administration" is meant delivery of the GPR91 agonists/antagonists or other compounds used in the methods herein, to the subject. Each administration method can occur with or without a pharmaceutical carrier or excipient, or with or without another therapeutic agent into the subject. Conventional and pharmaceutically acceptable routes of administration include, but are not limited to, systemic routes, such as oral, intraperitoneal, intravenous, intradermal, subcutaneous, and other parenteral routes of administration. Routes of administration may be combined, if desired. In some embodiments, the administration is repeated periodically.

"T1R3" (alternative name TAS1R3) is a G-protein-coupled receptor (GPCR) and a key component of the sweet and umami (amino-acid) heterodimeric receptors expressed primarily in taste cells and enteroendocrine cells of the gastrointestinal tract. T1R3 senses sugars and promotes hormone release to regulate insulin and glucose levels. A variety of compounds or compositions that can act as agonists or antagonists of T1R3 are known. See, e.g., the list of T1R3 ligand/modifiers described in International patent application publication No. WO2013/155142, incorporated by reference herein.

"Gustducin", as used herein, generally refers to the α-subunit of the heterotrimeric G protein which in taste cells, is formed by the association among Gα-gustducin (a Gα subunit), with a Gβ1 subunit and a Gγ13 subunit. It is also expressed in a number of extra-oral tissues, such as in the enteroendocrine cells of the gastrointestinal tract. Gα-gustducin is the major cellular downstream signaling element that couples with T1R3 and propagates the signal from activated receptor inside the cells. A variety of compounds or compositions that can act as agonists or antagonists of gustducin are known. See, e.g., the list of gustducin ligand/modifiers described in International patent application publication No. WO2013/155142, incorporated by reference herein.

"TRPM5" is the transient receptor potential cation channel subfamily M member 5, i.e., a cation channel that is essential for transduction of bitter, sweet and umami tastes. This gene that has been associated with metabolic syndrome, glaucoma, cirrhosis, pre-diabetes, and taste. Its human protein sequence is identified by GenBank Accession No. AAI43354.1; and encoded by the mRNA sequence identified by NCBI reference sequence NM_014555.3. Assays to identify compounds and compounds that enhance or inhibit this pathway are disclosed in U.S. Pat. No. 7,749,730 and International patent publication No. WO2009/045377, incorporated by reference herein.

Methods

In one aspect, a method involves administering to a mammalian subject at risk for, or having, an infection a composition or compound that stimulates the G protein receptor (Gpr91) pathway in intestinal cells to release IL-25 and enhance a type II immune response in the subject. The cells that are contacted with a compound or composition, e.g., a GPR91 agonist that stimulates GPR91 are generally mammalian intestinal cells. In one embodiment, these intestinal cells are tuft cells. In other embodiments, the cells contacted with a compound or composition includes other epithelial cells of the mammalian digestive system. In one embodiment, the subject is treated with succinate as described in the examples. In other embodiments, the compound or composition is a succinate analog or another agonist of GPR91.

In one embodiment of this method, the subject is treated by this method for an existing parasitic infection. By "parasitic infection" is included any infection the commonly affects the mammalian digestive system, such as a microorganism of the genus *Taenia, Diphyllobothrium, Hymenolepis, Dipylidium, Echinococcus,* or *Spirometra*. In one embodiment, the parasite is Giardia intestinalis, *Cryptosporidium parvum, Cyclospora cayetanensis* or *Isospora bello*. Still other known parasitic infections may be treated by the methods described herein. In still another embodiment, the subject is treated prior to infection with a parasite, such as when anticipating travel to an area in which exposure to parasites is anticipated.

In another embodiment of the method, the subject is treated for an existing bacterial infection. By "bacterial infection" is meant an infection of the gastrointestinal tract by bacteria such as *Yersinia, Staphylococcus, Shigella, Salmonella, Camplyobacter* and *E. coli*. In other embodiments the bacteria is *Clostridium difficile*. Still other bacteria that cause gastritis or other intestinal disorders are also expected to be treatable by GPR91 agonists/antagonists that stimulate GPR91 to cause tuft cells to produce IL-25, according to the methods described herein. In yet a further embodiment, the subject is treated prior to infection with a bacterium.

In still another embodiment of the method, the subject is treated for an existing microbial infection, e.g., fungal infection or infection by an amoeba, e.g., *Entamoeba histolytica*. In another embodiment, the subject is treated prior to infection with a fungus or other microorganism.

In another aspect, a method of treating ulcerative disorders of the intestines includes administering to a subject having an ulcerative disorder a composition or compound that blocks tuft cell-expressed Gpr91 or the Gpr91 pathway and inhibits release of IL-25. In one embodiment of this method, the disorder is Crohn's disease. In another embodiment of this method, the disease is Irritable Bowel Syndrome.

In still another aspect, a method of treating obesity also involves administering to an obese subject a composition or compound that stimulates the Gpr91 pathway in intestinal cells and releases IL-25.

In all of these methods, in addition to administering a GPR91 agonist/antagonist, an optional step includes administering to the subject a compound or composition that stimulates the gustducin pathway. Alternatively, an optional step includes administering to the subject a compound or composition that inhibits or antagonizes the gustducin pathway. In another embodiment, a method described herein further involves in addition to administering a GPR91 agonist/antagonist, an optional step includes administering to the subject a compound or composition that stimulates the T1R3 pathway. Alternatively, an optional step includes administering to the subject a compound or composition that inhibits or antagonizes the T1R3 pathway. In all of these methods, in addition to administering a GPR91 agonist/antagonist, an optional step includes administering to the subject a compound or composition that stimulates the TRPM5 pathway. Alternatively, an optional step includes administering to the subject a compound or composition that inhibits or antagonizes the TRPM5 pathway.

In each of the methods described herein, an active component, i.e., the GPR91 agonist/antagonist, and/or the gustducin agonist/antagonist, and/or the T1R3 agonist/antagonist, and/or the TRPM5 agonist/antagonist is delivered in a suitable pharmaceutical vehicle or formulation as described above to treat and/or prevent and/or inhibit the gastrointestinal disorders described herein.

The amount of the active composition or compound used in each method and present in each effective dose is selected with regard to consideration to the half-life of the compound, the identity and/or stage of the gastrointestinal disorder, the patient's age, weight, sex, general physical condition and the like. The amount of active component required to induce or inhibit an IL-25 mediated type II immune response without significant adverse side effects varies depending upon the pharmaceutical composition employed and the optional presence of other components. Generally, a useful therapeutic dosage is administered at a concentration of from and including dosages of from 40 mg/day to 120 mg/day active compound for adults. In one embodiment, the selected composition is administered in a single dose. In another embodiment an initial dose of a composition may be optionally followed by repeated administration for a duration selected by the attending physician.

Dosage frequency may also depend upon the factors identified above, and may range from 1 to 6 doses per day for a duration of about 3 days to a maximum of no more than about 1 week. The compositions may also be administered as a continuous infusion for about 3-5 days, the specific dosage of the infusion depending upon the half-life of the compound. The compounds may also be incorporated into other infection control protocols, involving repetitive cycles of dosing. Selection of the appropriate dosing method would be made by the attending physician.

In still other aspects aspect, cell-based methods are provided for identifying a compound that activates or initiates the GPR91 receptor in intestinal cells, resulting in type II immunity. One method for identifying a compound that activates or initiates type II immunity comprises using a tuft cell assay and contacting a tuft cell or cell line that expresses the G protein-coupled receptor GPR91 in vitro with a test compound; and assaying for a detectable change in the physical or functional characteristic of the contacted cells or cell lines in comparison to a reference cell or cell line control. The detectable change permits the determination that the test compound mimics the effect of dietary fat. In another embodiment, the cell or cell line also expresses the GPR91 protein.

In another aspect, a recombinant cell or cell line useful in such methods comprises a nucleic acid sequence or molecule that expresses GPR91 under the control of a suitable expression system, wherein said sequence or molecule is heterologous to the cell. In some embodiments, the nucleic acid sequences encoding the GPR91 proteins are homologs, or chimeric or modified versions of the naturally occurring Gpr91 and genes of a selected human or non-human mammal or animal.

All scientific and technical terms used herein have their known and normal meaning to a person of skill in the fields of biology, biotechnology, molecular biology and molecular genetics and by reference to published texts, which provide one skilled in the art with a general guide to many of the terms used in the present application.

EXAMPLES

The following examples are provided for the purpose of illustration only and the invention should in no way be construed as being limited to these examples but rather should be construed to encompass any and all variations that become evident as a result of the teaching provided herein.

Example 1: Succinate Induced Tuft Cell Hyperplasia

Figure 1B:
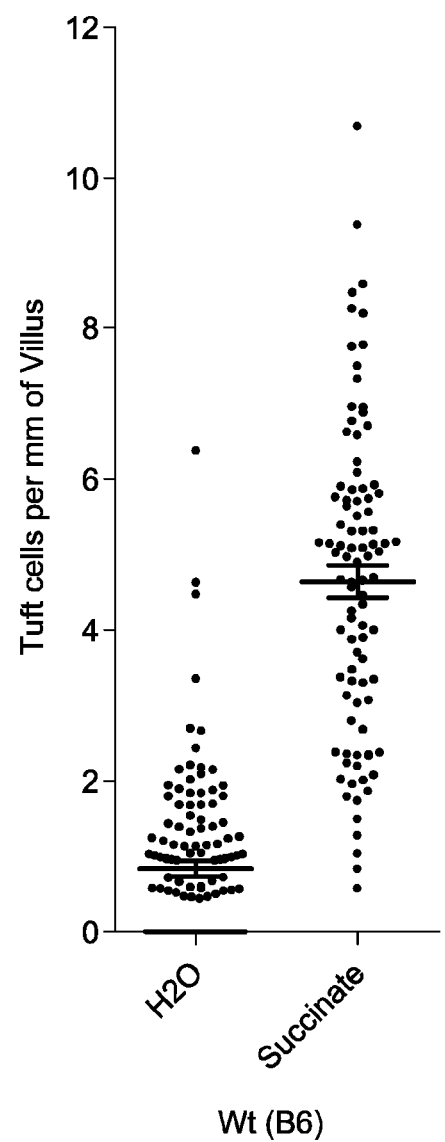
FIG. 1B demonstrates a statistical analysis of tuft cell expansion, which showed a significant increase in the number of tuft cells after succinate treatment (p<0.0001, t-test), i.e., a larger number of grey dots throughout the frame.

Wildtype B6 mice were provided with a drinking tube containing 100 mM succinate for 7 days. Then the intestinal tissues were analyzed for the presence of tuft cells using an antibody raised against Dclk1, a tuft cell marker. Tuft cell expansion was readily detectable in mice receiving succinate but not water (See FIGS. 1A and 1B).

Example 2: Succinate-Induced Tuft Cell Hyperplasia Requires Gustducin and Trpm5

To determine if tuft cell hyperplasia in response to succinate is mediated by transduction elements, the inventors provided gustducin knockout (KO) mice and Trpm5 KO mice with succinate-containing water (100 mM). Mice drank about the same amount of succinate-containing solutions as wildtype mice did. However, no expansion of tuft cells was observed in Trpm5 KO mice. There is a slight increase in the number of tuft cells in gustducin KO mice receiving succinate, which appears to be statistically significant.

Taken together, these data demonstrate that succinate activates tuft cell to regulate type 2 immunity, presumably via tuft cell-expressed Gpr91. Additionally, the inventors found tuft cell hypoplasia (i.e., a reduced number of tuft cells) in T1r3 knockout mice. This result indicates that tuft cell homeostasis may require T1r3. T1r3 may also recognize metabolites secreted from parasites or other microbes.

Example 3: Using Gpr91/SucnR1 Ligand Succinate for Treatment of Parasitic Infection For treatment of parasitic infection, mice are provided with free access to a drinking sprout containing 100 mM succinate (or other SucnR1 agonist) or plain water. Mice are then infected with intestinal parasites, such as *N. brasiliensis* or *Helgomosomoides polygyrus*. Mice are examined for the presence of worm (worm burden) in the small intestine, caecum, as well as feces for up to two weeks post-infection.

Similarly, the feces is examined for the presence of parasitic eggs.

It is anticipated that exogenous succinate acts on tuft cell-expressed Sucnr1 receptor (Gpr91) synergistically with succinate produced by helminthes to expand tuft cell hyperplasia and lead to expedited expelling of helminths from the body.

Succinate is also used as a dietary supplement to prevent worm infection. Succinate intake results in tuft cell hyperplasia and type 2 immunity. Thus, it can be used to prevent parasitic infection due to activated type 2 immunity.

Example 4—Using Gpr91/SucnR1 Ligand Succinate for Treatment of IBS, Crohns and IBD For treatment of irritable bowel syndrome (IBS), Crohn's disease, inflammatory bowel disease (IBD) and other potential GI disorders, a dextran sulfate sodium (DSS)-induced colitis mouse model is used to determine if targeting the succinate-Gpr91 axis results in clinical benefit for IBD disease. Mice are treated with DSS to induce intestinal damage. Mice are then provided with a drinking sprout containing 100 mM succinate or plain water. Gut tissue is collected and evaluated for the clinical and histological changes.

It is anticipated that succinate leads to better clinical outcome due to the beneficial effect of succinate-triggered type 2 immunity.

All publications cited in this specification in the reference section below and the above-noted U.S. provisional patent application No. 62/383,662 are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A method of treating ulcerative disorders of the intestines comprising administering to a subject having an ulcerative disorder a compound or composition thereof that blocks tuft cell-expressed Gpr91 or the Gpr91 pathway and inhibits release of IL-25.

2. The method according to claim 1, wherein the disorder is Crohn's disease or Irritable Bowel Syndrome.

3. The method according to claim 2, wherein the compound is a Gpr91 agonist.

4. The method according to claim 3, wherein the agonist is succinate or an analog thereof.

* * * * *